United States Patent [19]

Wilkinson, III et al.

[11] 4,434,136
[45] Feb. 28, 1984

[54] TAPERED-BOTTOM BLEACH CAKE FOR SANITATION DOSING DISPENSER

[75] Inventors: Randolph N. Wilkinson, III; Elmore C. Sneed, both of Cincinnati; Janet M. Mueller, Miamisburg, all of Ohio

[73] Assignee: The Proctor & Gamble Company, Cincinnati, Ohio

[21] Appl. No.: 355,983

[22] Filed: Mar. 8, 1982

[51] Int. Cl.³ ............................................. B01D 11/02
[52] U.S. Cl. ............................ 422/263; 4/227; 4/228; 134/93; 210/198.1; 222/185; 222/424.5; 422/266
[58] Field of Search ............... 422/261, 263, 264, 265, 422/266, 271, 279, 277; 4/227, 228, 231; 248/226.5; 134/93, 36; 252/90, 93, 95, 174.23; 210/206, 749, 198.1; 222/185, 424.5

[56] References Cited

U.S. PATENT DOCUMENTS

| | | | |
|---|---|---|---|
| 2,387,944 | 10/1945 | Raymond | 134/93 X |
| 2,538,720 | 1/1951 | Wood | 422/264 B X |
| 2,984,841 | 5/1961 | Wilson | 4/231 |
| 2,985,377 | 5/1961 | Saeks | 4/231 X |
| 3,088,126 | 5/1963 | Klingler | 4/231 |
| 3,234,141 | 2/1966 | Robson | |
| 3,521,306 | 7/1970 | Jacobs | 4/228 |
| 3,946,902 | 3/1976 | Stepanek, Jr. | 422/264 B X |
| 3,998,751 | 12/1976 | Murray | |
| 4,053,429 | 10/1977 | Tatara et al. | |
| 4,108,792 | 8/1978 | Farmer, Jr. | |
| 4,113,645 | 9/1978 | De Simone | |
| 4,145,306 | 3/1979 | Tatara et al. | |
| 4,171,546 | 10/1979 | Dirksing | 4/228 |
| 4,186,856 | 2/1980 | Dirksing | 222/424.5 |
| 4,192,763 | 3/1980 | Buchan | |
| 4,200,606 | 4/1980 | Kitko | 422/37 |
| 4,208,747 | 6/1980 | Dirksing | 4/228 |
| 4,216,027 | 8/1980 | Wages | 134/36 |
| 4,246,129 | 1/1981 | Kacher | 252/90 |
| 4,247,070 | 1/1981 | Dirksing | 248/226.5 |
| 4,248,827 | 2/1981 | Kitko | 422/37 |
| 4,251,012 | 2/1981 | Williams | 222/185 |
| 4,253,951 | 3/1981 | McCune | 210/749 |
| 4,281,421 | 8/1981 | Nyquist et al. | 4/228 |
| 4,283,300 | 8/1981 | Kurtz | 252/95 |
| 4,302,350 | 1/1981 | Callicott | 252/174.23 |

FOREIGN PATENT DOCUMENTS 5286 11/1979 European Pat. Off.

Primary Examiner—Richard L. Chiesa
Attorney, Agent, or Firm—Richard C. Witte; Ronald L. Hemingway; Leonard Williamson

[57] ABSTRACT

A tapered-bottom bleach cake for a sanitation dosing dispenser provides more even delivery of bleach sanitizer in automatic sanitization of flush toilet and thereby reduces bleach waste.

7 Claims, 6 Drawing Figures

TAPERED-BOTTOM BLEACH CAKE FOR SANITATION DOSING DISPENSER

TECHNICAL FIELD

The most specific technology to which this invention relates is that of disinfecting devices adapted to dispense disinfectant solutions to the tank of a conventional toilet when it is flushed.

BACKGROUND ART

Dispensers which are adapted to deliver disinfecting or aesthetic ingredients to a toilet tank to condition water in the toilet tank and bowl are known.

The following commonly-owned references will serve as background art for dosing dispensers and cakes of active ingredients used in combination therewith, and are incorporated herein by reference:

U.S. Pat. No. 4,171,546, Dirksing, issued Oct. 23, 1979;
U.S. Pat. No. 4,208,747, Dirksing, issued June 24, 1980;
U.S. Pat. No. 4,186,856, Dirksing, issued Feb. 5, 1980;
U S. Pat. No. 4,216,027, Wages, issued Aug. 5, 1980;
U.S. Pat. No. 4,200,606, Kitko, issued Apr. 29, 1980;
U.S. Pat. No. 4,248,827, Kitko, issued Feb. 3, 1981;
U.S. Pat. No. 4,253,951, McCune, issued Mar. 3, 1981;
U.S. Pat. No. 4,246,129, Kacher, issued Jan. 20, 1981;
U.S. Pat. No. 4,251,012, Williams, issued Feb. 17, 1981;
U.S. Pat. No. 4,247,070, Dirksing, issued Jan. 27, 1981;
U.S. Pat. No. 4,302,350, Callicott, issued Nov. 24, 1981;
U.S. Pat. No. 4,281,421, Nyquist et al, issued Aug. 4, 1981;
U.S. Pat. No. 4,283,300, Kurtz, issued Aug. 11, 1981; and
European Pat. Appln. 0,005,286, Nyquist, published Nov. 14, 1979.

Hypochlorite cakes of various shapes for dosing dispensers are disclosed in European Pat. Application, Ser. No. 0,005,286, Nyquist, published Nov. 14, 1979; but Nyquist does not teach that cake "shape" is a means for controlling the concentration of hypochlorite solution dispensed with each flush cycle within the context of a specified dispenser.

U.S. Pat. No. 4,208,747, Dirksing, issued June 24, 1980, discloses highly effective toilet tank dispensers which receive a dose volume of water from a toilet tank in which such a dispenser is placed every time the toilet is flushed. This patent teaches that cleaning and disinfecting cakes can be used in such dispensers, but fails to address the specific problems posed by certain types of cakes, particularly when hypochlorite cakes are placed inside the reservoir of such a toilet tank dispenser. FIGS. 9–14 and 18 of U.S. Pat. No. 4,208,747, Dirksing, disclose "top-feed" dispensers in which hypochlorite cakes are completely immersed in the dosing liquid in the reservoir and in which the solution is drawn from above of the cake. Such cake/dispenser combinations do not deliver a consistent amount of available chlorine over the life of the cake. Dirksing also discloses a dosing dispenser of the "bottom-feed" type illustrated by FIGS. 1–8 and 15–17. Symmetrical rectangular-shaped cakes are used therein. In such dispensers the bleach cake is only partially immersed in dosing liquid in the reservoir.

The present invention includes a "bottom-feed" dosing dispenser.

It has been discovered that a problem with a symmetrical rectangular-shaped bleach cake prism in a bottom-feed dosing dispenser is that it delivers significantly nonuniform concentrations of hypochlorite solutions over the life of the cake. Specifically, more concentrated hypochlorite solutions are dispensed during the first few days of usage which results in a waste of the hypochlorite chemical.

It is an object of the present invention to reduce hypochlorite chemical waste in bottom-feed hypochlorite dispensers.

It is another object of the present invention to provide a dosing dispenser containing a new water-soluble calcium hypochlorite cake which dissolves and gravity feeds into the dispenser reservoir water to provide a more uniform concentration of hypochlorite solution for each dispensing cycle.

Another object of the present invention is to provide a dosing dispenser containing a water-soluble hypochlorite cake which saves chemicals and thereby reduces cost.

These and other objects of the present invention will become apparent in the light of the following disclosure.

SUMMARY OF THE INVENTION

This invention is a dosing dispenser containing a solid water-soluble calcium hypochlorite cake within a reservoir means, said dispenser including means for allowing a dose volume of water to be routed through the reservoir with each dispensing cycle and means for immersing a lowermost portion of said cake to a predetermined depth in said water to facilitate dissolving a portion of said hypochlorite for dispensing at a later time. The cake of this invention is substantially completely water-soluble. The cake exhibits a geometric form that is of nonuniform cross-sectional area, as measured along at least a portion of its vertical height. The cross-sectional area of the cake generally increases in the direction of increased vertical height, whereby the lowermost surface area of the cake immersed in the water increases as the cake dissolves and gravity feeds into the water. The dispenser of this invention provides a substantially uniform concentration of hypochlorite solution for each dispensing cycle for the life of the cake. The preferred hypochlorite bleach cake exhibits a generally rounded tapered bottom.

BRIEF DESCRIPTION OF THE DRAWINGS

While the specification concludes with claims particularly pointing out and distinctly claiming the present invention, it is believed that the present invention will be better understood from the following description in conjunction with the accompanying drawings in which:

DETAILED DESCRIPTION OF THE INVENTION

Figure 1:
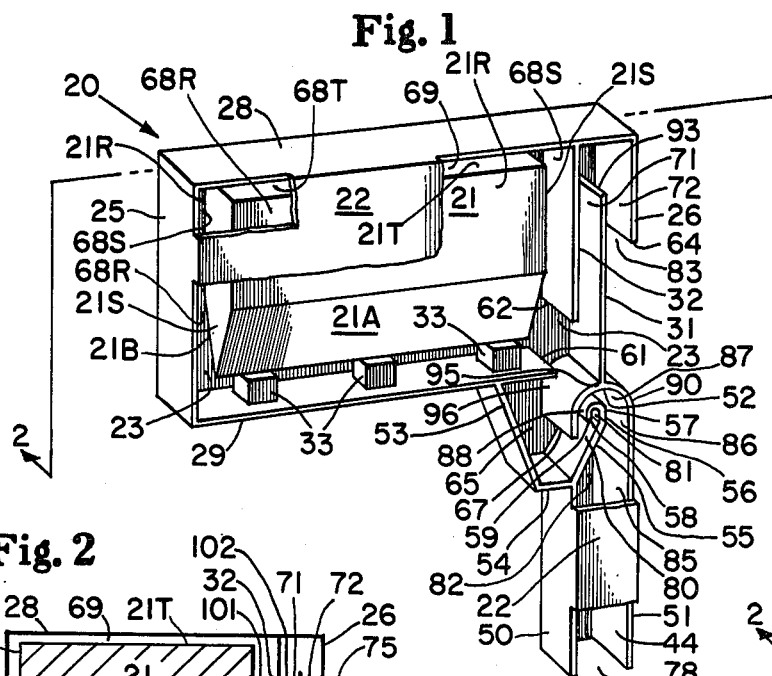
FIG. 1 is a partially torn away perspective view of an automatic bottom-feed passive dosing dispenser containing a solid cake with a taper which is used to illustrate the present invention.

The present invention comprises a dosing dispenser containing a water-soluble calcium hypochlorite cake within a reservoir, said dispenser including means for allowing a dose volume of water to be routed through said reservoir with each dispensing cycle and means for immersing the lowermost portion of said cake to a predetermined depth in said water to facilitate dissolving a portion of said hypochlorite for dispensing at a later time, the improvement wherein said cake is substantially completely water-soluble and exhibits a geometric form that is of nonuniform cross-sectional area, as measured along at least a portion of its vertical height, said cross-sectional area of said cake generally increasing in the direction of increased vertical height, whereby the surface area of said cake immersed in said water increases as said cake dissolves and gravity feeds into said water to provide a substantially uniform concentration of hypochlorite solution with each dispensing cycle.

Cakes having preferred nonuniform cross-sectional areas are illustrated by the tapered-bottom cakes shown in FIGS. 1, 2, 3 and 6. As shown, the tapered bottom can be rounded or generally sharpened or pointed. It can be a single wedged taper or a symmetrical double wedged taper.

The solid cake can be comprised of any suitable material which provides the hypochlorite anion ($OCl^-$) in aqueous solution. Such materials can comprise alkaline metal and alkaline earth metal hypochlorites, hypochlorite addition products, chloramines, chlorimines and chloramides. Specific examples of compounds of this type include sodium hypochlorite, potassium hypochlorite, lithium hypochlorite, calcium hypochlorite, calcium hypochlorite dihydrate, monobasic calcium hypochlorite, dibasic magnesium hypochlorite, chlorinated trisodium phosphate dodecahydrate, potassium dichloroisocyanurate, sodium dichloroisocyanurate, sodium dichloroisocyanurate dihydrate, 1,3-dichloro-5,5-dimethylhydantoin, N chlorosulfamine, chloramine T dichloramine T chloramine B, and dichloramine B. Preferred cakes comprise calcium hypochlorite and/or a swelling control salt selected from the group consisting of lithium hypochlorite, lithium chlorite, lithium hydroxide, potassium sulfate and mixtures thereof.

The dosing dispenser of this invention is typically placed into the water tank of a toilet. The dispenser has means for receiving a dose volume of water from the flush tank of the toilet. The received water is routed to a reservoir within the dispenser which contains the calcium hypochlorite cake. The tapered cakes of this invention are for a bottom-feed dispenser. The dispenser has means for immersing a lowermost portion of the cake to a predetermined depth in the received water to facilitate dissolving a portion of the hypochlorite for dispensing at a later time The cake is sized to initially occupy most of the allotted cake compartment space within the dispenser reservoir. The cake and the cake compartment preferably have parallel cake surfaces and compartment walls. It is important that there is at least 0.4 cm to 4 cms of free space between the vertical cake surfaces and the corresponding compartment walls. The free space is more preferably 0.5 cm to 2 cms. The dispenser retains the hypochlorite solution in substantial isolation from the body of toilet tank water during quiescent periods in between flushes. The dispenser also has means for releasing the hypochlorite solution from the dispenser into the tank water in the flush tank when the water drains from the tank into the toilet bowl during flushing. Available chlorine typically at a level of from about 2 parts per million (ppm) to about 10 ppm is provided in the toilet bowl water. The solid cake composition of this invention is formulated to slowly dissolve and "gravity feed" into the reservoir of the dispenser and disappear after numerous flushes.

The preferred tapered calcium hypochlorite cake of this invention is a tableted solid comprising: (I) an effective amount of a water-soluble calcium hypochlorite cake swelling control salt selected from the group consisting of lithium hypochlorite material (Form 2 ®), lithium hydroxide, lithium sulfate hydrate, lithium chloride and equivalent calcium hypochlorite swelling control salts, and mixtures thereof; and (II) from about 10% to about 98% of a substantially stable calcium hypochlorite material containing from about 65% to about 78% (i) calcium hypochlorite and (ii) the balance being a mixture of salts and other by-product materials normal to the manufacture of calcium hypochlorite.

Cake Preparation

The compacted solid calcium hypochlorite cake compositions of this invention may be prepared by conventional compacting procedure. For example, granules of calcium hypochlorite, e.g., HTH ®, and granules of the selected salts (such as described above) are mixed together, and this mixture is then pressed into a cake with a compacting machine. The granules are generally in a size range of from about 50 microns to about 1,000 microns prior to compacting. The compacted solids can also be formed by tabletting, "slugging," Chilsonating, or otherwise converting the granular hypochlorite mixture into compacted forms.

The tapered compacted solids can be formed, for example, in a conventional tabletting machine. The granular calcium hypochlorite and granular salts are initially weighed and then dry mixed to produce a homogeneous mixture. This resulting mixture is then stamped into a tablet, i.e., a compact cake. Compacting may be accomplished at pressures of from about 0.5 tons/square inch to about 200 tons/square inch, preferably from about 1.0 tons/square inch to about 50 tons/square inch, and most preferably from about 1.5 tons/square inch to about 5.0 tons/square inch. The compacting can be done on any conventional compacting apparatus, e.g., a Stokes Model R Tablet Press. The compacted cakes generally have a specific gravity of about 1.3 to about 2.3, preferably from about 1.5 to about 2.0.

The cake is formed into shapes with overall dimensions appropriate to fit the reservoir cake chamber or compartment of the gravity feed dosing dispenser. The reservoir cake compartment can also exhibit a tapered bottom.

The preferred cake of this invention is generally a rectangular shaped prism with a tapered bottom. Cake overall height is preferably 70 mm to 85 mm. Cake thickness from tapered bottom to top is 1 mm to 20 mm, preferably above the taper the thickness is 12 mm to 20 mm. Cake width from tapered bottom to top is 1 mm to 50 mm, preferably above the taper the width is 35 mm to 50 mm. Free space between the cake surfaces and the cake compartment walls must be enough to allow for some cake swelling due to hydration when put in use. The free space as measured generally along any perpendicular line between opposite vertical cake surfaces and parallel corresponding cake compartment walls is at least 4 mm to 40 mm, and preferably from 5 mm to 20 mm.

Method of Use

Figure 2:
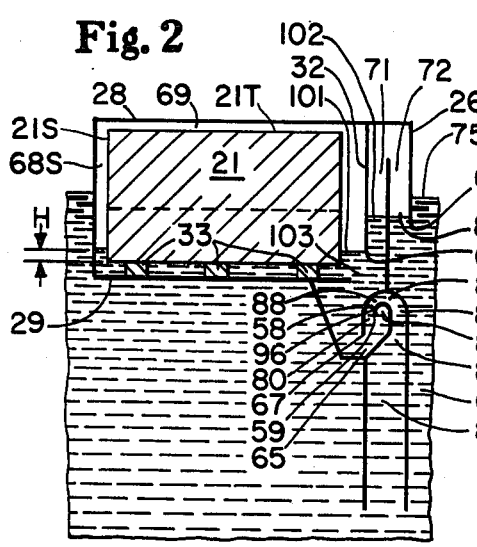
FIG. 2 is a simplified sectional view which shows a portion of a cycle of the dispenser shown in FIG. 1 and which view is taken along section line 2—2 of FIG. 1.

The dosing dispenser of this invention is used as a disinfectant chlorine source in flush toilets. The compacted compositions are placed within a dispenser which is used within the flush tank of the toilet. An operable "gravity feed" dispenser is shown in FIGS. 1 and 2. The compacted cakes should be of a size to fill from about 50% to about 90% of the volume of the cake compartment surrounding the cake. Preferably about 50% to about 70%. Some unoccupied free space is needed to accommodate cake swelling upon contact with water. Sufficient cross-sectional free space between the cake and the dispenser cake compartment walls is important to avoid "cake hang-up" which results in wasted chemical.

A dose volume of toilet tank water is introduced into the dispenser during a normal water rise in the flush cycle of the toilet, contacting the cake composition in the dispenser. This water remains in the dispenser in contact with the lower portion of the cake. About 0.5% to 20%, preferably 1% to 5%, of the total surface area of the cake is initially exposed to the water within the dispenser. During the time between flushes a portion of the hypochlorite dissolves in the water, thereby forming a relatively concentrated solution of hypochlorite. When the toilet is flushed, a dose of concentrated hypochlorite solution is discharged into the toilet bowl along with substantially all the water in the flush tank.

Cake swelling control is desirable in the context of a dissolving cake in a bottom-feed dispenser. The degree of swelling that can be tolerated depends on the size of the cake relative to the size of the dispenser reservoir housing the cake which determines product life and functionality.

Calcium Hypochlorite

The calcium hypochlorite raw material for the purpose of the present invention is preferably a solid, dry calcium hypochlorite granular material containing at least about 65% by weight of calcium hypochlorite and about 5% of water, the balance being materials usually resulting from the process of manufacture, e.g., sodium chloride, calcium hydroxide, chloride and carbonate. In a reported practice of calcium hypochlorite manufacture, the calcium hypochlorite is obtained as a slurry containing crystals of calcium hypochlorite dihydrate [$Ca(OCl)_2.2H_2O$] in a mother liquor consisting essentially of an aqueous solution of calcium hypochlorite and sodium chloride. The slurry is filtered on a rotary vaccum filter to produce a cake that retains sufficient mother liquor to have a moisture content of 45% to 50% by weight. The wet cake, e.g., from an Eimco Filter, when dried directly yields the 70% calcium hypochlorite of commerce. However, if a higher concentration of calcium hypochlorite is desired, the wet cake may be washed with water to remove some of the mother liquor and then filtered or centrifuged or otherwise processed to separate further quantities of liquid and to form a wet solid which on drying produces granules which contain from about 85% to about 90% by weight of calcium hypochlorite.

The calcium hypochlorite content of the calcium hypochlorite granules used in formulating compositions of this invention is generally at least about 60% and preferably ranges from about 65% to about 75% by weight. The compound calcium hypochlorite contains about 100% available chlorine, thus a composition containing 65% calcium hypochlorite contains about 65% available chlorine. Commercial calcium hypochlorite material usually contain at least about 65% available chlorine, i.e., 71% to 73% of calcium hypochlorite, 20% byproducts, and about 5% water. A commercial calcium hypochlorite containing about 65% to about 72% available chlorine is marketed under the name "HTH" by Olin Mathieson Chemical Corporation. A typical analysis of HTH ® is as follows:

| Ingredient | Typical Weight % |
|---|---|
| Calcium hypochlorite $Ca(OCl)_2$ | 70–75 |
| Sodium chloride NaCl | 4–23 |
| Calcium hydroxide $Ca(OH)_2$ | 1.5–5 |
| Calcium carbonate $CaCO_3$ | 1.0–5 |
| Calcium chlorate $Ca(ClO_3)_2$ | 0.4–4 |
| Calcium chloride $CaCl_2$ | 0.5–3 |
| Water | 0.4–8.5 |

Processes for preparing calcium hypochlorite material may be found in U.S. Pat. No. 3,953,354, Faust, issued Apr. 27, 1976; U.S. Pat. Nos. 3,639,284, Long et al., issued Feb. 1, 1972; and 3,560,396, Robson, issued Feb. 2, 1971. Various calcium hypochlorite compositions contain varying amounts of $Ca(OCl)_2$ as indicated herein.

Swelling Control Salts

The solid cake compositions of this invention preferably contain an effective amount of a swelling control salt. "Swelling control salts" means water-soluble salts other than calcium hypochlorite which are compatibly incorporated into calcium hypochlorite cake compositions and provide improved swelling for the cake over cakes made of essentially commercial grade calcium hypochlorite material, such as HTH. Swelling control salts are selected inorganic salts which are not reactive to hypochlorite bleach and provide improved swelling of calcium hypochlorite material. Examples of preferred swelling control salts include lithium hypochlorite, lithium hydroxide, lithium sulfate, lithium sulfate hydrate, lithium chloride, and mixtures thereof.

An effective amount of swelling control salt in a typical calcium hypochlorite cake composition can range from about 1% to about 90% by weight of the cake, preferably a cake composition contains from about 2.5% about 40% of added swelling control salt.

The choice of swelling control salts will affect the hydration and swelling of the compacted cake on its initial exposure to the aqueous environment within the dispenser. To minimize cake swelling and improve dissolution of the disinfecting composition, preferred calcium hypochlorite cake compositions include "Form 2" and sodium chloride. Lithium hypochlorite, the preferred swelling control salt, can be obtained as a pure compound, but is preferably obtained in its commercially available form referred to herein as "Form 2", which contains from about 30% to about 40% of pure lithium hypochlorite with the balance being inorganic diluents and moisture. The pure compound lithium hypochlorite contains about 120% available chlorine, thus a composition containing 10% lithium hypochlorite receives about a 12% available chlorine contribution from the lithium hypochlorite component. A commercial lithium hypochlorite, marked with U.S. Pat. No. 3,171,184, contains about 36% available chlorine and is marketed under the trade name "Form 2" by the Lithium Corporation of America. A typical analysis of "Form 2", as reported by the manufacturer, is as follows:

| ELEMENTAL ANALYSIS | | | |
|---|---|---|---|
| | | Weight % | |
| Ingredient | Typical | Maximum | Minimum |
| Available chlorine | 36 | 38 | 35 |
| Lithium hypochlorite | 30 | 31 | 29 |
| Lithium | 4.5 | 5.3 | 3.5 |
| Sodium | 18 | 22 | 14 |
| Potassium | 3 | 6 | 2 |
| Chlorides (total) | 45 | 55 | 34 |
| Sulfates | 11 | 22 | 5 |
| Chlorates | 2 | 4 | 1 |
| Carbonates | 1.5 | 3 | 0.5 |
| Chlorites | 0.1 | 0.5 | 0.05 |
| Hydroxides | 0.5 | 1 | 0.2 |
| Water | 7 | 9 | 4 |
| TRACE METALS | | | |
| Metal | Typical | | Maximum |
| Iron | 7 ppm | | 20 ppm |
| Copper | 1 ppm | | 2 ppm |
| Nickel | 0.1 ppm | | 0.5 ppm |
| Mercury | 0.05 ppm | | 0.1 ppm |
| Lead | 0.5 ppm | | 1 ppm |
| Arsenic | 0.1 ppm | | 0.5 ppm |
| Zinc | 1.5 ppm | | 3.0 ppm |
| CHEMICAL ANALYSIS | | | |
| | | Weight % | |
| Ingredient | Typical | | Guaranteed |
| Available chlorine | 36 | | 35 |
| LiOCl (active ingredient) | 30 | | |
| NaCL | 34 | | |
| Na$_2$SO$_4$ and K$_2$SO$_4$ | 20 | | |
| LiCl | 3 | | |
| LiClO$_3$ | 3 | | |
| LiOH | 1 | | |
| Li$_2$CO$_3$ | 2 | | |
| H$_2$O | 7 | | |
| PHYSICAL PROPERTIES: | | | |
| Bulk Density: | Loose, 58 lbs/cu.ft. | | |
| | Packed, 65 lbs/cu.ft. | | |
| Particle Size, | | | |
| U.S. Standard Sieves: | Standard, −10+ 70 | | |
| | Special, −10+ 20, −20+ 50 | | |

Processes for preparing lithium hypochlorite compositions are found in U.S. Pat. Nos. 2,590,794, Robson, issued Mar. 25, 1952; 2,534,781, MacMahon, issued Dec. 19, 1950; and 3,171,814, Orazem et al., issued Mar. 2, 1965. The term "lithium hypochlorite" used in the specification and claims includes commercially available lithium hypochlorite material, such as Form 2. Various lithium hypochlorite compositions contain varying amounts of LiOCl, as indicated herein.

The preferred cake of this invention comprises "HTH" calcium hypochlorite and "Form 2" at a weight ratio of from 3:2 to 19:1, and most preferably 3:2 to 9:1. Another preferred cake comprises "HTH" and lithium sulfate hydrate at a weight ratio of from 1:9 to 49:1, most preferably 19:1. Cake compositions of this invention can comprise "HTH" and lithium hydroxide at a ratio of 4:1 to 19:1, preferably 9:1. Sodium chloride can be present in the cakes at levels up to 50%.

The following salts exhibit cake swelling control: Form 2 is most preferred due to its available chlorine content and excellent swelling control properties; also preferred are lithium sulfate hydrate; lithium hydroxide; and lithium chloride.

Table I shows a list of preferred ranges of HTH/salt cake composition ratios that exhibit swelling control.

TABLE I

| Salt | Most Preferred HTH/Salt | % Confidence* | Less Preferred HTH/Salt | % Confidence* |
|---|---|---|---|---|
| Form 2 | 90:10 to 60:40 | 99 or more | 95:5 to 90:10 | 90 |
| Li$_2$SO$_4$ H$_2$O | 95:5 to 10:90 | 97.5 or more | 98:2 to 95:5 | 95 |
| LiOH | 90:10 to 80:20 | 99 or more | 95:5 to 90:10 | 90 |

*This tells how confident one can be judging from statistical test, i.e., that the ratio of HTH/salt is effective in swelling control.

Tapered vs. Rectangular Bleach Cakes

Figure 3:
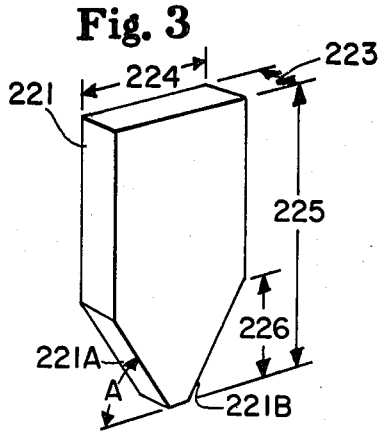
FIGS. 3, 4 and 6 are perspective views of four different geometric forms of solid hypochlorite cakes of this invention.
Figures 4, 5:
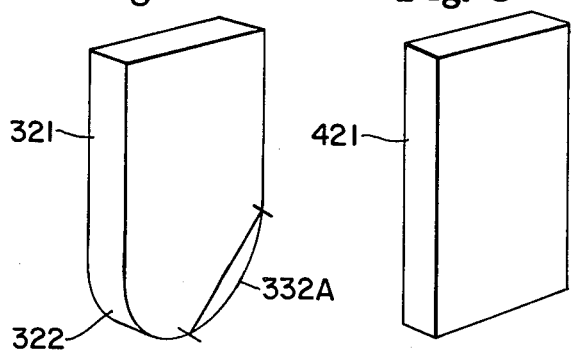
FIG. 5 is a prior art cake.

The hypochlorite delivery performances of two types of tapered cakes (FIGS. 3 and 4) were compared with the performance of the prior art symmetrical cake illustrated in FIG. 5. The characteristics of the three types of cakes are set out in Table II.

TABLE II

| | Cake Characteristics | | |
|---|---|---|---|
| | Cake Shape | | |
| | Symmetrically Rectangular | Tapered Round | Tapered Sharp |
| Weight (g) | | | |
| Avg. | 54.07 | 54.05 | 54.03 |
| Std. Dev. | 0.03 | 0.03 | 0.09 |
| Width (mm) | | | |
| Avg. | 39.99 | 39.97 | 39.96 |
| Std. Dev. | 0.04 | 0.03 | 0.02 |
| Thickness (mm) | | | |
| Avg. | 18.94 | 18.89 | 18.87 |
| Std. Dev. | 0.10 | 0.08 | 0.04 |
| Height (mm) | | | |
| Avg. | 43.64 | 49.34 | 56.83 |
| Std. Dev. | 0.61 | 0.35 | 0.43 |
| Density (g/cc) | 1.74 | 1.74 | 1.74 |
| Composition (%) | | | |
| Ca(OCl$_2$) HTH ® | 80 | 80 | 80 |
| LiOCl Form 2 ® | 9 | 9 | 9 |
| NaCl | 11 | 11 | 11 |

Referring to FIG. 3 for the tapered sharp cake the angle "A" was about 60°. Referring to FIG. 4 for the tapered round cake the arc length 332a was about 30 mm. The test description, equipment and results are described below. The tapered cakes were superior to the rectangular cake in uniform delivery of active. See Table III.

Test Description

Eight replicates of each type of cake were tested. All cakes were of the same weight, width, thickness, density and composition. Only their heights differed to obtain equal weights. They were all sealed in the same kind of bottom-feed dispensers similar to the one shown in FIGS. 1 and 2. A complete description of each cake is given in Table II.

Test Equipment

All 24 dispensers were placed in an automatic flush tank timed to flush 10 times per day in 60° F. (16° C.) water. Samples of hypochlorite solutions for each were collected every day (including weekends) at the 2:45 PM flush and titrated idiometrically to determine the grams of Av. $Cl_2$ dispensed. The grams dispensed at the 2:45 PM flush is taken as representative of the average dispensed per day. Consequently, for this test, the readings obtained were multiplied by ten to obtain grams dispensed per day. Additionally, of the eight measurements taken for each cake, the high and low measurements were deleted and the average of the remaining six were recorded in Table III. Photographs were also taken daily to determine when the tapers disappeared. The tapers disappeared on the 6th day.

TABLE III

Avg. Grams of Av. $Cl_2$ Dispensed vs. Time for Rectangular vs. Tapered Cakes

| Day | Rectangular | Tapered Round | Tapered Sharp |
|---|---|---|---|
| 1 | 2.73 | 1.57 | 2.00 |
| 2 | 2.57 | 1.90 | 1.68 |
| 3 | 1.90 | 1.32 | 1.69 |
| 4 | 1.87 | 1.34 | 1.37 |
| 5 | 1.56 | 1.24 | 1.05 |
| 6 | 1.04 | 1.05 | 1.17 |
| 7 | 1.28 | 0.93 | 1.29 |
| 8 | 1.49 | 1.21 | 1.15 |
| 9 | 1.65 | 1.30 | 1.22 |
| 10 | 1.40 | 1.28 | 1.34 |
| 11 | 1.29 | 1.52 | 1.63 |
| 12 | 1.62 | 1.48 | 1.36 |
| 13 | 1.10 | 1.23 | 1.48 |
| 14 | 0.65 | 0.84 | 0.91 |
| 15 | 0.82 | 1.18 | 1.45 |
| 16 | 0.77 | 1.17 | 1.27 |
| 17 | 0.38 | 0.96 | 1.27 |
| 18 | 0.14 | 0.73 | 1.13 |
| 19 | 0.05 | 0.39 | 0.62 |
| 20 | — | 0.27 | 0.72 |
| 21 | — | 0.07 | 0.34 |
| 22 | — | — | 0.10 |

As is shown in Table III, the tapered cakes significantly reduced the concentration of Av. $Cl_2$ dispensed for the first five days. It was also noted that the tapers disappeared around the sixth day. A cake is considered used up when less than 0.1 gram is dispensed per day. Table III shows that the tapered round and sharp cakes, respectively, lasted 3 and 4 days longer than the rectangular cake. These data clearly show that a tapered cake performs more efficiently, delivering active more consistently and more uniformly, than a rectangular cake within the context of the present invention.

DETAILED DESCRIPTION OF THE DRAWINGS

Referring now to FIGS. 1 and 2 in which identical features are identically designated, FIG. 1 shows a preferred bottom-feed dispenser 20. The dispenser 20 contains a solid state calcium hypochlorite bleach cake 21, also referred to herein as the solid water-soluble product 21. Dispenser 20 comprises a front wall 22, a back wall 23, sidewall segments 25 and 32 which constitute the cake compartment; other dispenser walls include walls 31, 50, 51 and 90, a top wall 28, bottom wall segments 29, 53 and 54, and interior partitions 32, 55, 56, 57, 58, 95 and 96, and solid product support members 33. The solid product support members 33 are of lesser thickness than the width of the dispenser to ensure that liquid can wash across part of the tapered lowermost surfaces 21a and 21b of solid product 21 along its entire length. The walls and partitions are rigid and define a liquid solution reservoir 65 for a liquid solution, a cake compartment 69, a siphon tube 44 having a second air trap 82 disposed adjacent thereof and having discharge reservoir 85, uppermost vertical passageway 86, a horizontal passageway 87, a vertical passageway 88 connecting with inlet/discharge conduit 80, said inlet/discharge conduit having a first air trap 81 disposed adjacent thereto, and vent means for the reservoir comprising passageways 71 and 72 and air vent 83. The lowermost edge of partition segment 58 is designated 59, the lowermost edge of partition segment 96 is designated 67, the exposed edge of bottom wall segment 29 is designated 61, the lowermost edge of level control partition 32 is designated 62, the uppermost edge of sidewall segment 31 is designated 93, and the lowermost edge of sidewall segment 26, which in conjunction with front and back walls 22 and 23, respectively, and sidewall segment 31 define air vent 83, is designated 64. The inlet/discharge port of dispenser 20 located at the lowermost end of siphon tube 44 is designated 78. The free spaces 68R–68S around the cake 21 within cake compartment 69 is designed to accommodate some cake swelling upon initial contact with water 63. If free space 68 is too small, the cake 21 when swollen will hang up on the walls 22, 23, 25 and level control partition wall 32 and the hung up cake will be wasted.

The depth of immersion, i.e., water exposed cake surface area of cake 21 is controlled by the vertical distance "H" between the uppermost surface of product support members 33 and lowermost edge 62 of level control partition 32. The amount of interface between the cake and the liquid contained within the dispenser 20 controls the solid hypochlorite cake 21 dissolution rate. With dispenser embodiments of the type generally shown in FIG. 1 it has generally been found that the vertical distance "H" should be less than about 1 cm, and most preferably less than about 0.5 cm.

An exemplary dispenser embodiment (not shown) of the present invention employing two shelf-like support members secured to and projecting from back wall 23, each of said support members having an overall height of about 15 mm, as measured from bottom wall segment 29, and an uppermost surface area of approximately 0.35 square inch each. Preferred is a larger reservoir (not shown) centrally positioned under two support members 33. A vertical distance "H" of about 10 mm between the uppermost surface of the support members and the lowermost edge of the level control partition can be employed.

The solid product in question initially can weigh about 60 grams and have a lowermost surface measuring 5 cms in length by about 1.27 cms in width.

Referring to FIG. 2, when the dispenser 20 containing a calcium hypochlorite solid product 21 is disposed, for instance, in a toilet tank (not shown) on a bracket or other mounting means (not shown) so that the FULL level of water 63 in the toilet tank is sufficiently high to at least reach edge 64 of sidewall segment 26, the dispenser will respond as the level of water drops from the FULL position in the toilet tank when the toilet is flushed and thereafter as the level of water in the toilet tank rises to the FULL position after completion of the flush cycle. The flush cycle is fully shown and explained in said U.S. Pat. No. 4,208,747.

Referring to FIG. 2 it is apparent that reservoir 65 will retain a portion of the concentrated hypochlorite product solution 103 after the dispensing operation is completed. The hypochlorite solution 103 thus retained will be available to cover rapid multiple flushes of the toilet and preferably is larger than shown, and/or a secondary reservoir (not shown) can be designed in bottom wall 29. Secondary solution reservoirs (not shown) can be designed to collect insoluble cake by-products of hypochlorite solution 103 in the lowermost portions of primary solution reservoir 65.

When the level of the toilet tank water 63 is in the FULL position, as illustrated in FIG. 2, the dispenser 20 will likewise be restored to the condition illustrated in FIG. 2 and will remain in that condition during the ensuing quiescent period awaiting the next flush cycle of the toilet.

The dispenser embodiment 20 illustrated in FIGS. 1 and 2 can discharge a predetermined quantity or dose-volume of hypochlorite product solution 103 from the dispenser each time the toilet is flushed. The dose-volume of solution is substantially equal to the quantity of solution contained within dispenser 20 between lowermost edge 62 of level control partition 32 and lowermost edge 67 of partition segment 96 in addition to the column of product solution contained within passageway 71. The amount of hypochlorite product solution 103 that can be dispensed during each flush cycle is more easily understood by comparing FIG. 2, which illustrates the condition of the dispenser 20 when the toilet tank water level 75 is FULL and air vent 83 has been blocked by the water, with FIG. 1, which illustrates the condition of an empty dispenser when the solution level within solution reservoir 65 would be at lowermost edge 67 of partition segment 96 and the dose-volume of solution has been released through inlet/outlet port 78.

The solid, water-soluble calcium hypochlorite cake product 21 contained in cake compartment 69 will dissolve in the water introduced during each flush cycle to form the hypochlorite product solution 103 until such time as the solution becomes saturated or the toilet is again flushed. As the lower portions of the cake 21 are consumed by exposure to the liquid, the solid product will feed towards support members 33 and wall 29 within cake compartment 69. Because the volume and exposed surface area of cake 21 below edge 62 of level control partition wall 32 remain essentially constant throughout the life of the solid product, the strength or concentration of the hypochlorite solution 103 is particularly controlled throughout the life of the dispenser 20, assuming an adequately long quiescent period for the solution to reach a normal concentration level is provided intermediate the flush cycles, i.e., about 4 hours between flushes. It should be obvious that a shorter quiescent period, up to the saturation point, will result in a hypochlorite solution 103 that will be correspondingly less concentrated with less dissolved solid product 21.

While the exemplary embodiment of dispenser 20, may be constructed by adhesively securing sections of relatively rigid Plexiglas (Registered Trademark of Rohm and Haas Company) to one another, other relatively rigid materials which are substantially inert with respect to the intended product and aqueous solutions thereof can be used to construct the dispensers. Furthermore, the dispensers may be constructed or formed at high speed and relatively low cost utilizing various manufacturing techniques well known in the art. For example, the dispensers could be vacuum thermoformed in two sections of a material such as polyvinyl chloride having an initial thickness of about 0.5 mm to about 1 mm, the solid, water-soluble product inserted therebetween and the two sections thereafter secured to one another as by heat sealing, adhesives, etc.

The dispenser 20 in FIG. 1 is shown prior to the charging operation, i.e., before it is immersed in toilet tank water 63 as shown in FIG. 2. In a flush cycle (not shown) the toilet tank water 63 rises, it enters siphon tube 44 and discharge reservoir 85 through inlet/discharge port 78. Air within the upper reaches of the siphon tube 44 is allowed to vent through discharge reservoir 85, vertical passageway 86, horizontal passageway 87, vertical passageway 88, inlet/discharge conduit 80, liquid solution reservoir 65, vent passageways 71 and 72 and air vent 83. As the level of the toilet tank water 63 continues to rise, it begins to enter horizontal passageway 87. Because the difference in elevation of the water in the toilet tank and the water within the siphon tube is relatively small prior to air vent 83 becoming blocked, the water head or water pressure available to force the water in siphon tube 44 around the loop through vertical passageway 88 and into inlet/discharge conduit 80 is likewise quite small. To minimize the required driving force to initiate water flow through the loop, the dispenser 20 preferably employs a series of passageways 86, 87 and 88, each of which is smaller in cross-section than any portion of the one immediately preceding it, thereby providing capillary suction in the direction of flow which tends to draw the water from the siphon tube 44 into the inlet/discharge conduit 80. It is of course recognized that a maximum degree of capillary suction may be provided by employing passageways 86, 87 and 88 which are tapered and exhibit a continued reduction in cross-section in the direction of liquid flow during the dispenser charging operation. If desired, the entire length of the siphon tube 44 above the discharge reservoir 85 may be convergent in the direction of water flow during the charging operation.

Once toilet tank water 63 enters inlet/discharge conduit 80 and begins to collect in the solution reservoir 65, air is trapped in air trap 81 disposed adjacent inlet/discharge conduit 80 (not shown). Namely, an air bubble is retained within the confines of the air trap 81 defined by partition segments 55, 56, 57 and 58, which condition persists as long as toilet tank water 63 continues to enter the dispenser 20.

Referring again to FIG. 2, when the level 101 of incoming liquid within dispenser cake compartment 69 reaches lowermost edge 62 of level control partition 32, an air-lock is formed in the uppermost reaches of the cake compartment 69, thereby preventing the liquid from rising further within the cake compartment 69. It should be noted that the liquid contacts only a lower surface area of cake 21 up to a predetermined cake height "H" up to lowermost edge 62.

In the event the FULL level of the toilet tank is below the air vent 83, the level 102 of hypochlorite product solution 103 in passageway 71 will be identical to the level 75 of the toilet tank water 63 surrounding the dispenser, while the level 101 of product solution 103 within cake compartment 69 will be controlled by lowermost edge 62 of level control partition 32.

In the event level control partition 32 is eliminated and the FULL level of the toilet tank is below the air vent 83, the level of product solution 103 within the dispenser 20 will be identical to the level 75 of toilet tank water 63 surrounding the dispenser 20. In all cases, dispenser 20 will function to isolate the resultant hypochlorite solution 103 contained in the upper reaches of cake compartment 69 from the surrounding toilet tank water 63, whether or not air vent 83 is blocked by toilet tank water. In the event air vent 83 is blocked by toilet tank water, isolation is provided by means of an air-lock created in the upper reaches of passageway 72 in conjunction with the air-lock created in horizontal passageway 87. In the event air vent 83 is not blocked by toilet tank water, the vent to atmosphere provides the desired isolation from the toilet tank water 63.

Referring again to FIG. 2, which represents the condition of the dispenser 20 when the toilet tank water level 75 is in its FULL position, the bulk of the air bubble retained within air trap 81 during the charging operation has rotated about edge 59 of partition segment 58 so as to substantially fill horizontal passageway 87 as well as the uppermost portions of vertical passageways 86 and 88, thereby isolating the resultant liquid hypochlorite product solution 103 contained within the inlet/discharge conduit 80 from the toilet tank water 63 contained within passageway 86 of siphon tube 44. The resultant hypochlorite product solution 103 contained within passageway 71, cake compartment 69, solution reservoir 65 and inlet/discharge conduit 80 is completely isolated from toilet tank water by means of the air-lock provided in the uppermost sections of passageways 71 and 72 and the air-lock provided in the uppermost sections of vertical passageways 86 and 88 and horizontal passageway 87.

As will be appreciated by those skilled in the art, the toilet tank water 63 brought into contact with solid calcium hypochlorite cake 21 during the charging operation will continue to dissolve the cake 21 at least until such time as the hypochlorite product solution 103 becomes saturated or until such time as the toilet is flushed and a predetermined quantity or dose-volume of the liquid hypochlorite product solution 103 is available for dispensing and is either completely or partially discharged. As will also be appreciated by those skilled in the art, the exterior surfaces of solid calcium hypochlorite product 21 are preferably so configured as to permit a uniform delivery of hypochlorite solution 103 over the life of the calcium hypochlorite cake product 21. To this end, the exterior surfaces of the solid cake product 21 are tapered at the bottom to offset the effect of relatively high initial solubility of a fresh cake. Cake 21 and the cakes of FIGS. 3, 4 and 6 all show preferred tapered cakes. FIGS. 3 and 4 show the more preferred cakes.

Transfer of hypochlorite product solution 103 from the solution reservoir 65 into the discharge reservoir 85 to be discharged through the inlet/discharge port 78 continues until such time as the solution level in solution reservoir 65 reaches edge 67 of partition segment 96 (not shown), thereby venting siphon tube 44 and allowing the product solution 103 contained therein to be released into the toilet tank water 63.

The discharge reservoir 85 preferably comprises an enlarged end of the siphon tube 44. The discharge reservoir 85 and its associated inlet/discharge port or ports 78 can be sized to provide for discharging of the hypochlorite solution 103 at almost any point in the flush cycle and at almost any rate of discharge.

The solid calcium hypochlorite cakes of this invention do not form gels, but do form a small amount of insoluble by-products comprising calcium carbonate. So, dispensers having support members 33 are preferred to ensure that insoluble particles are washed away. The support members 33 positioned in the lowermost portion of the cake compartment 69 support the cake 21 and are a level control means to control the liquid level in contact with the cake 21. Said support members 33 also help to prevent the insoluble particles from building up on and around the hypochlorite cake. The support members 33 also serve to control the area of contact between the liquid contained within the dispenser reservoir and the cake 21.

So long as liquid is routed through the product chamber during each flush cycle of the toilet, the cake insoluble by-products will continue to be dispersed into the hypochlorite liquid solution and which ultimately settles into the solution reservoir 65 located generally beneath the cake compartment 69. Accordingly, the tendency of the insoluble cake by-products to build up on and around the cake is minimized.

With particularly preferred dispenser embodiments of the present invention, the discharge of the bulk of the liquid hypochlorite product solution generally occurs just before the completion of the flush cycle before the toilet tank discharge outlet is closed and before tank refill begins.

The dispenser disclosed herein is particularly well suited for use with other component products particularly if they are isolated from each other prior to use. Each dispenser section of such a plural product dispenser will also maintain each product component in isolation from the toilet tank water and simultaneously dispense the products when the toilet is flushed. Such plural product dispensing embodiments could be fabricated as a single unit suspended in the toilet tank independently of one another, or interdependently suspended in the toilet tank by means of a common bracket or the like. Because the constant volume of solution dispensed during each flush cycle may readily be determined, it is thus possible to size such plural product dispensers so that each of the product components will be completely consumed at about the same point in time, thereby minimizing waste of any particular component.

Tapered Cakes

Referring now to FIG. 3, solid cake 221 illustrates a preferred hypochlorite bleach cake which exhibits symmetrical side tapers 221a and 221b. Cake 221 has a total height of 3 inches (7.62 mm) a taper height of 1.2 inches (30.5 mm), a top width of about 1.55 inches (39.4 mm), a bottom width of about 3.8 mm and the taper forms an angle of about 60° from the horizontal. The tapers 221a and 221b preferably form angles of from about 30° to about 65° from the horizontal, but is functional over a wider range. Cake thickness 223 is preferably 12 mm to 20 mm; cake width 224 is preferably 35 mm to 50 mm and the cake overall height 225 is preferably about 70 mm to 85 mm. The cake taper height 226 of tapers 221a and 221b is preferably about 25% to about 50% of the total cake height 225, but is functional over a wider range.

Referring now to FIG. 4, another preferred cake 321 shows a rounded bottom taper 322. This preferred cake 321 has thickness, height and width geometry which is generally the same as that of cake 221, except for the geometry of the taper 322. The rounded bottom taper 322 has an arc length 332a of about 30 mm. In preferred cakes of similar geometry, the arc of the rounded bottom may vary from about 20 mm to about 50 mm.

FIG. 5 is a rectangular prism-shaped cake 421 with a square bottom.

Figure 6:
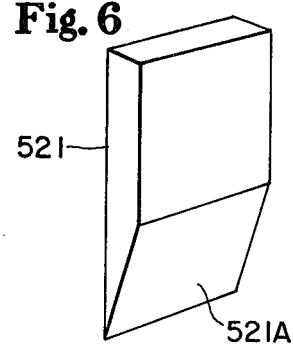

FIG. 6 is a perspective view of a tapered cake 521 with one taper 522.

While particular embodiments of the present invention have been illustrated and described, it will be obvious to those skilled in the art that various changes and modifications can be made without departing from the spirit and scope of the invention and it is intended to cover, in the appended claims, all such modifications that are within the scope of this invention.

What is claimed is:

1. A toilet tank dosing dispenser containing a solid cake of water-soluble calcium hypochlorite within a reservoir cake compartment, said dispenser including means for allowing a dose volume of water to be routed through said reservoir with each dispensing cycle and means for immersing a lowermost portion of the cake to a predetermined depth in said water to facilitate dissolving a portion of said cake for dispensing at a later time; wherein said water level drops below said cake with each dose;

characterized in that:

said cake being substantially completely water-soluble and having a geometric form that is of nonuniform cross-sectional area, as measured along at least a portion of its vertical height, said cross-sectional area generally increasing in the direction of increased vertical height, whereby the amount of cross-sectional area of said lowermost portion immersed in said water increases as said vertical height decreases, said cake and said reservoir cake compartment containing sufficient free space to allow the cake to gravity feed by dissolution into said water; said dosing dispenser providing a substantially uniform concentration of hypochlorite solution for each dispensing cycle for the life of the cake.

2. The invention of claim 1 wherein said cake exhibits a generally tapered bottom, and wherein a lower portion of said taper is immersed in said water.

3. The invention of claim 1 wherein said cake exhibits a rounded tapered bottom, and wherein a lower portion of said rounded taper is immersed in said water.

4. The invention of claim 1 wherein said cake exhibits a generally sharp tapered bottom, and wherein a lower portion of said sharp taper is immersed in said water.

5. The invention of claim 1 wherein said cake generally has a thickness of 12 mm to 20 mm, a cake top width of 35 mm to 50 mm, an overall height of 70 mm to 85 mm and a specific gravity of 1.5 to 2.0, and wherein said free space as measured generally along perpendicular lines between upper cake surfaces and corresponding walls of said cake compartment as 4 mm to 20 mm.

6. The invention of claims 1, 3 or 5 wherein said tapered bottom is rounded and has a round bottom arc length of 20 mm to 30 mm.

7. The invention of claims 4 or 5 wherein said tapered bottom exhibits a sharp taper having a taper angle of 30° to 65°.

* * * * *